US00PP35802P2

(12) United States Plant Patent
Whitaker

(10) Patent No.: US PP35,802 P2
(45) Date of Patent: May 14, 2024

(54) STRAWBERRY PLANT NAMED 'FL 18.52-66'

(50) Latin Name: ***Fragaria* x *ananassa* Duchesne**
Varietal Denomination: FL 18.52-66

(71) Applicant: Florida Foundation Seed Producers, Inc., Marianna, FL (US)

(72) Inventor: Vance Whitaker, Brandon, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,221

(22) Filed: Jun. 2, 2023

Related U.S. Application Data

(60) Provisional application No. 63/475,138, filed on Oct. 17, 2022.

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

PP30,564 P3 6/2019 Whitaker
PP33,477 P2 9/2021 Whitaker

*Primary Examiner* — Susan McCormick Ewoldt
(74) *Attorney, Agent, or Firm* — Koenig IP Works, PLLC; Katherine Koenig

(57) ABSTRACT

A new and distinct variety of strawberry (*Fragaria* x *ananassa*), which originated from seed produced by a hand-pollinated cross between 'FL 13.27-142' and 'FL 16.78-94'. The new strawberry, named 'FL 18.52-66', can be distinguished at least by its white internal fruit color when fully ripe; white external fruit color with a pink blush and red achenes when fully ripe; consistent conical shape; and moderate acid content when grown in West Central Florida or other regions that have a climate similar to that of West Central Florida.

2 Drawing Sheets

Genus and species: *Fragaria* x *ananassa* Duchesne.
Cultivar denomination: 'FL 18.52-66'.

BACKGROUND OF THE NEW CULTIVAR

The present invention relates to a new and distinct cultivar of strawberry plant (*Fragaria* x *ananassa* Duchesne) named 'FL 18.52-66.' This new strawberry plant is distinguished at least by its ability to produce fruit that have white internal color and white external color with a pink blush when fully ripe, consistent conical shape, and an intense flavor including moderate acid content when grown in West Central Florida. Asexual propagation of 'FL 18.52-66' was performed at Balm, Florida, which is also where the selection was made and the plants were tested. 'FL 18.52-66' can be contrasted with 'Florida Brilliance' (U.S. Plant Pat. No. 30,564), the current, dominant strawberry variety in Hillsborough County and 'FL 16.78-109' (U.S. Plant Pat. No. 33,477), the first white-fruited strawberry variety grown commercially in the region. 'FL 18.52-66' is a promising candidate for commercial success because it produces fruit that are white with light pink blush and red achenes when fully ripe throughout the entire Florida market window.

Plant Breeder's Rights for this cultivar have not been applied for. The new strawberry cultivar 'FL 18.52-66' has not been made publicly available more than one year prior to the filing of this application.

SUMMARY OF THE INVENTION

The new strawberry cultivar 'FL 18.52-66' has not been observed under all possible environmental conditions. The phenotype of the new cultivar may vary with variations in environment and cultural practices such as temperature, light intensity, fertilization, irrigation, and application of plant growth regulators without any change in genotype.

'FL 18.52-66', when grown in a subtropical climate during the fall, winter, or a combination thereof, can be distinguished from all other strawberry plants by at least the following characteristics: white internal fruit color when fully ripe; white external fruit color with a pink blush and red achenes when fully ripe; consistent conical shape; and moderate acid content.

'FL 18.52-66' originated in a strawberry breeding plot in Balm, Florida. The seed parent was 'FL 13.27-142', an unreleased, unpatented breeding selection with excellent fruit firmness, shape and disease resistance. The pollen parent was 'FL 16.78-94', an unreleased, unpatented breeding selection with white internal color and white to light pink external color when ripe. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 18.52-66' was selection number 66 of the $52^{nd}$ cross in the 2018-2019 seedling trial, and thus was given the breeding trial designation of 'FL 18.52-66.' 'FL 18.52-66' exhibited unique white to fruit color with a pink blush when fully-ripe, excellent shape and intense flavor. 'FL 18.52-66' has been asexually propagated annually by runners; and test plantings have established that the vegetative and fruit characteristics of the propagules are identical to those of the initial daughter plants.

'FL 18.52-66' can be distinguished from its seed parent 'FL 13.27-142' at least by its white fruit color with red achenes as compared with the red fruit color and yellow achenes of the seed parent. 'FL 18.52-66' can also be distinguished from its pollen parent 'FL 16.78-94' at least by its larger fruit size (approximately 20% greater than the pollen parent) and greater firmness (approximately 30% greater than the pollen parent).

Currently, 'Florida Brilliance' (U.S. Plant Pat. No. 30,564) is the dominant strawberry variety in Hillsborough County, Florida. 'FL 18.52-66' can be distinguished from 'Florida Brilliance' due to its white fruit color with a pink blush when fully ripe (FIG. 1) as compared to the medium red fruit color of 'Florida Brilliance'. 'FL 18.52-66' can be distinguished from 'FL 16.78-109' by its greater acid content (approximately 31-69% greater than 'FL 16.78-109' (Table 1)) leading to a unique, intense flavor and its more consistent fruit size, resulting in approximately half the number of small, unmarketable fruit (<10 grams) as compared to 'FL 16.78-109' (Table 2).

'FL 18.52-66' is more resistant to Phytophthora root and crown rot (caused by *Phytophthora cactorum*) than both commercial standards.

DESCRIPTION OF THE FIGURES

The accompanying photographs illustrate the overall appearance of the new strawberry cultivar 'FL 18.52-66'. These photographs show the colors as true as can be reasonably obtained in colored reproductions of this type. Colors in the photographs may differ slightly from the color values cited in the detailed botanical description, which accurately describe the colors of the new strawberry cultivar.

DETAILED BOTANICAL DESCRIPTION OF THE CULTIVAR

Figure 1:
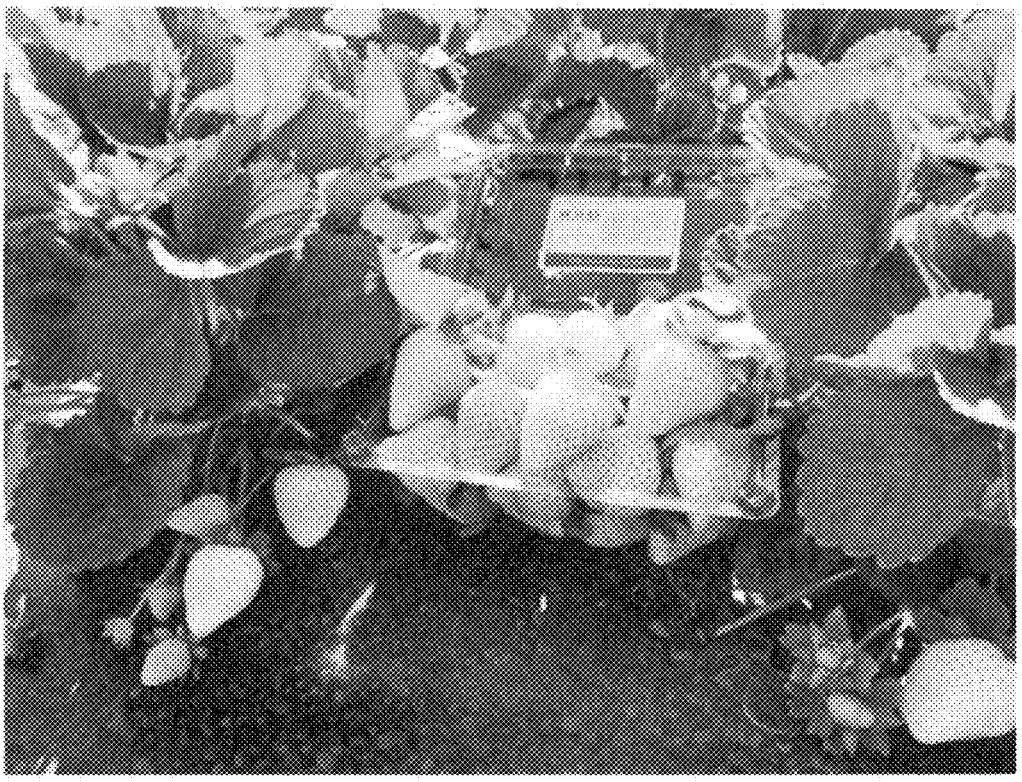
FIG. 1 shows unripe and ripe fruit of the new strawberry cultivar as disclosed herein, showing white flesh with a pink blush and red achenes from five-month-old specimens in February 2021, near Balm, Florida.
Figure 2:
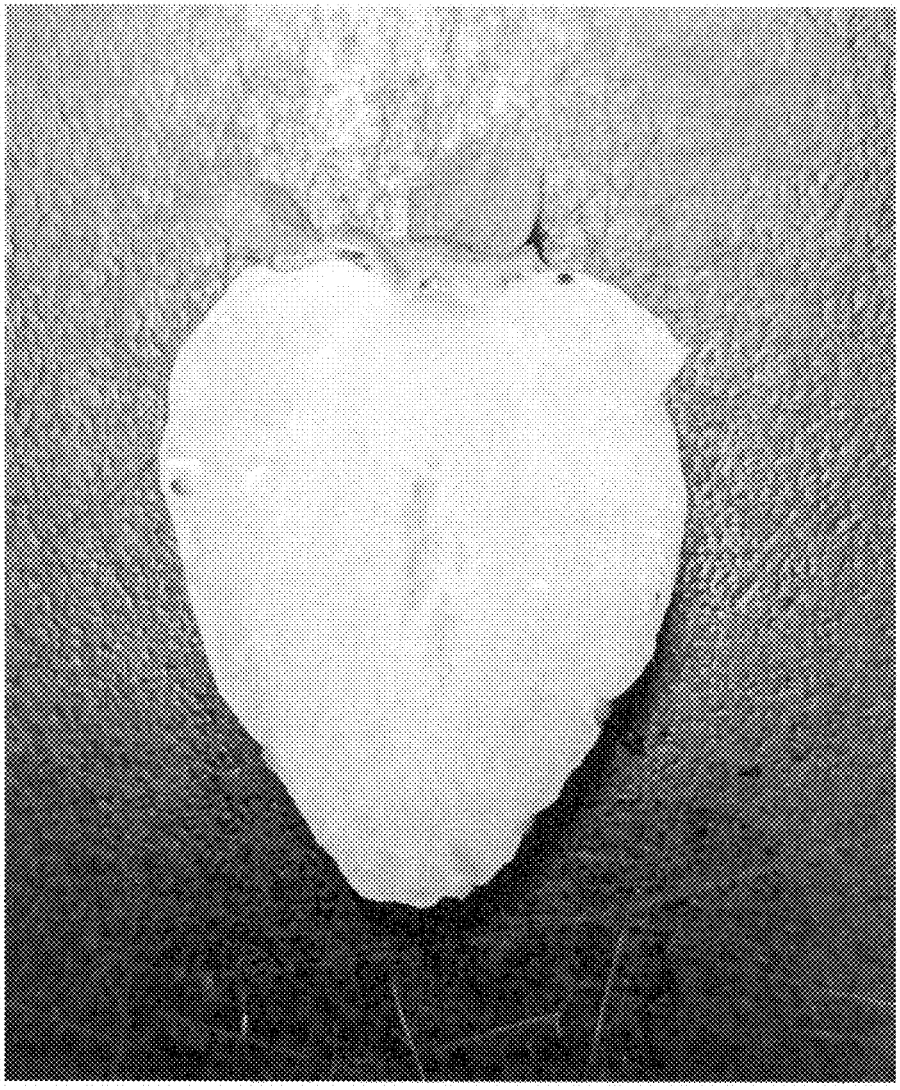
FIG. 2 shows a cross-sectional image of a ripe fruit of the new strawberry cultivar as disclosed herein, showing white flesh.

The following detailed botanical description sets forth the distinctive characteristics of 'FL 18.52-66'. The present botanical description is of 'FL 18.52-66' when grown under the ecological conditions that prevail during the winter production season in Balm, Florida, i.e., warm days and cool nights. Colors are objectively described using the CIELAB color scale (originally published by the International Commission on Illumination (CIE) in 1976) as measured using a MINOLTA® Chroma Meter CR-400 (JMM Lee Properties, LLC, Burbank, California) colorimeter with a 1-cm aperture, calibrated against a white tile (Y=85.5, x=0.3164, y=0.3237). When the CIELAB color designations differ from the accompanying photographs, the CIELAB color designations are accurate.

Botanical Description

Botanical classification:
- *Family*.—Rosaceae.
- *Botanical name*.—*Fragaria* x *ananassa* Duchesne.
- *Common name*.—Strawberry.
- *Cultivar*.—'FL 18.52-66'.

Parentage:
- *Female or seed parent*.—'FL 13.27-142'.
- *Male or pollen parent*.—'FL 16.78-94'.

Plant description:
- *Growth habit*.—Moderately compact, round.
- *Average height*.—18 cm to 26 cm.
- *Average width*.—18 cm to 23 cm.
- *Number of crowns per plant*.—4 to 7, depending on seasonal conditions.
- *Vigor*.—Medium.

Foliage description:
- *Overall description*.—Pinnately compound with three leaflets.

Petiole:
- *Average length*.—14.0 cm.
- *Average diameter*.—2.7 mm.
- *Pubescence*.—Light.
- *Pubescence density*.—Light.
- *Pose of hairs*.—Perpendicular.
- *Texture*.—Smooth.
- *Anthocyanin presence*.—Absent.
- *Color*.—Pale green (L*=34.94, a*=−14.81, b*=19.11).

Petiolule:
- *Length*.—Terminal leaflet: 5.0 mm. Lateral leaflets: 4.3 mm.
- *Diameter*.—1.9-2.1 mm.
- *Color*.—Light green (L*=53.79, a*=−12.78, b*=31.45).

Stipule:
- *Length*.—28 mm to 32 mm.
- *Width*.—10-14 mm along the base of the petiole attachment.
- *Anthocyanin presence*.—Occasional.
- *Color*.—Light green (L*=60.81, a*=−2.21, b*=23.37).

Terminal leaflet:
- *Average length*.—65 mm.
- *Average breadth*.—61 mm.
- *Length/width ratio*.—1.07.
- *Shape in cross section*.—Slightly concave to flat.
- *Color, upper surface*.—Medium green (L*=34.73, a*=−15.08, b*=19.13).
- *Color, lower surface*.—Light green (L*=55.27, a*=−12.28, b*=16.75).
- *Glossiness*.—Slight gloss.
- *Base shape*.—Cuneate.
- *Apex descriptor*.—Rounded.
- *Pubescence density*.—Sparse.
- *Texture*.—Moderately smooth.
- *Venation pattern*.—Pinnate.

Secondary leaflets:
- *Average length*.—58 mm.
- *Average breadth*.—57 mm.
- *Length/width ratio*.—1.02.
- *Shape in cross section*.—Slightly concave to flat.
- *Color, upper surface*.—Medium green (L*=34.25, a*=−14.78, b*=18.95).
- *Color, lower surface*.—Light green (L*=50.54, a*=−12.44, b*=17.31).
- *Glossiness*.—Slight gloss.
- *Base shape*.—Oblique rounded.
- *Apex descriptor*.—Obtuse.
- *Pubescence density*.—Sparse.
- *Texture*.—Moderately smooth.
- *Venation pattern*.—Pinnate.

Leaflet margins: Crenate, with an average of 22 and 22 serrations per terminal and secondary leaflet, respectively.

Stolons:

*Number of daughter plants.*—20 to 35 depending on environmental conditions.

*Anthocyanin presence.*—Absent.

*Thickness.*—2 mm to 2.5 mm.

*Pubescence.*—Light.

Inflorescence:

*Time of flowering.*—Partial remontancy, commencing two weeks after establishment and continually thereafter in suitable climate.

*Flower number per plant.*—45 to 60 flowers over a 4 month Florida growing season.

*Flower height.*—0 to 17 cm above soil surface depending on angle of pedicel.

*Position relative to canopy.*—Flowers open at or slightly below canopy height.

*Branching of the inflorescence.*—At or within 3 cm of the crown.

Petals:

*Shape.*—Orbicular.

*Apex.*—Rounded.

*Base.*—Rounded.

*Margin.*—Smooth.

*Number.*—5 to 6.

*Length.*—12 mm to 13 mm.

*Width.*—Approximately 13 mm.

*Average diameter of the corolla* (*i.e. the petals collectively*).—31.5 mm.

*Average number of stamens.*—24.

Calyx:

*Insertion of calyx.*—Level to slightly inserted.

*Diameter.*—Approximately 39 mm.

*Diameter of calyx relative to corolla.*—Approximately 1.2.

*Diameter of calyx relative to the fruit.*—Approximately 1.3.

*Color.*—Medium green (L*=36.30, a*=16.30, b*=20.31).

Sepals:

*Margin.*—Smooth.

*Number per flower.*—10 to 11.

*Length.*—10 mm to 15 mm.

*Width.*—8 mm to 10 mm.

*Apex.*—Variable, rounded to acute.

*Color, upper surface.*—Medium green (L*=36.30, a*=16.30, b*=20.31).

*Color, lower surface.*—Light green (L*=48.57, a*=15.27, b*=21.87).

Pedicels: Attached to mature primary fruit, 7 cm to 13 cm in length and 1.7 mm and 2.0 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:

*Number per truss.*—5 to 8.

*Shape.*—Medium conical to cordate.

*Average fruit weight.*—18 to 21 g.

*Weight, primary fruit.*—21 to 32 g.

*Weight, secondary and tertiary fruit.*—13 to 19 g.

*Length, primary fruit.*—42 mm to 52 mm.

*Width, primary fruit.*—28 mm to 37 mm.

*Fruit flavor.*—Intense, moderately acidic.

*Fruit soluble solids content* (*brix*).—As high as 9.4% in January 2021 at UF GCREC (Table 1).

*Fruit cavity.*—Rare.

*Achenes.*—Slightly sunken, 50 to 150 per fruit, at least 75% of which are red in color.

*External fruit color.*—White with light pink blush (a*=2.30).

*Internal fruit color.*—White (a*=2.41).

*Evenness of color.*—Pink blush on sun side, most achenes red in color.

*Flesh and skin firmness at full ripe stage.*—Very firm.

*Rain damage.*—Similar to 'FL 16.78-109'.

Yield: Lower than 'Florida Brilliance' in total but higher during some months than 'FL 16.78-109' (Table 2).

Preferred planting period: October 5th to October 20th in West Central Florida.

Nursery performance: 'FL 18.52-66' produces slightly similar numbers of runners to 'Florida Brilliance'.

Disease resistance:

*Botrytis fruit rot* (*caused by Botrytis cinerea*).—Moderately susceptible.

*Powdery mildew* (*caused by Podosphaera aphanis*).—Moderately resistant.

*Anthracnose fruit rot* (*caused by Colletotrichum acutatum*).—Moderately susceptible.

*Charcoal rot* (*caused by Macrophomina phaseolina*).—Moderately resistant.

TABLE 1

Soluble solids content (SSC), pH, titratable acidity (TA), and SSC/TA from three harvest dates.

| Cultivar | SSC (%) | pH | TA (%) | SSC/TA |
|---|---|---|---|---|
| | | January 2021 | | |
| FL Brilliance | 8.80 b[z] | 3.70 b | 0.79 b | 11.20 b |
| FL 16.78-109 | 10.07 a | 3.96 a | 0.68 b | 14.93 a |
| FL 18.52-66 | 9.41 ab | 3.70 b | 0.89 a | 10.58 b |
| | | February 2021 | | |
| FL Brilliance | 6.49 a | 3.70 b | 0.64 b | 10.09 b |
| FL 16.78-109 | 6.78 a | 3.92 a | 0.49 c | 14.09 a |
| FL 18.52-66 | 7.23 a | 3.62 b | 0.83 a | 8.67 c |
| | | March 2021 | | |
| FL Brilliance | 6.30 b | 3.75 b | 0.60 a | 10.70 b |
| FL 16.78-109 | 7.19 a | 3.97 a | 0.48 b | 15.87 a |
| FL 18.52-66 | 7.06 a | 3.72 b | 0.67 a | 10.53 b |

[z]Mean separations within harvest dates and columns are by Tukey's HSD test, $P \leq 0.05$.

TABLE 2

Marketable yield and proportion of small fruit grown in Wimauma, Florida, during the 2020-21 season.

| | Marketable yield (g/plant) | | | |
|---|---|---|---|---|
| Cultivar | November | December | January | February |
| | | 2020-21 | | |
| FL Brilliance | 3.2 a | 48.8 a | 114.2 a | 473.1 a |
| FL 16.78-109 | 1.7 a | 15.6 b | 37.2 c | 442.7 a |
| FL 18.52-66 | 8.4 a | 23.2 b | 73.4 b | 439.7 a |
| | | 2021-22 | | |
| FL Brilliance | 3.4 a | 79.1 a | 372.6 a | 554.0 a |
| FL 18.52-66 | 3.3 a | 37.7 b | 263.3 b | 368.8 b |

TABLE 2-continued

Marketable yield and proportion of small fruit grown in Wimauma, Florida, during the 2020-21 season.

| Cultivar | Marketable yield (g/plant) March | Total 2020-21 | Small (%)[z] |
|---|---|---|---|
| FL Brilliance | 189.5 a | 1044.3 a | 7.9 b |
| FL 16.78-109 | 169.2 a | 810.5 b | 15.5 a |
| FL 18.52-66 | 175.5 a | 873.6 b | 8.6 b |

TABLE 2-continued

Marketable yield and proportion of small fruit grown in Wimauma, Florida, during the 2020-21 season.

| | 2021-22 | | |
|---|---|---|---|
| FL Brilliance | 145.1 a | 1154.0 a | 3.5 b |
| FL 18.52-66 | 138.9 a | 812.0 a | 9.0 a |

[z]Small fruit were defined as those less than 10 g and were considered non-marketable. The number of small fruit are expressed as a percentage of total fruit harvested.
[y]Mean separation within columns is by Tukey's HSD test, $P \leq 0.05$.

What is claimed is:

1. A new and distinct strawberry plant named 'FL 18.52-66' as illustrated and described herein.

* * * * *